US010835346B2

(12) United States Patent
Bellows et al.

(10) Patent No.: US 10,835,346 B2
(45) Date of Patent: *Nov. 17, 2020

(54) BRAKE ASSEMBLY FOR MEDICAL DEVICE SUPPORT SYSTEM

(71) Applicant: American Sterilizer Company, Mentor, OH (US)

(72) Inventors: Lance Clark Bellows, Painesville, OH (US); Christopher Roy Mohr, Mentor, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/517,703

(22) Filed: Jul. 22, 2019

(65) Prior Publication Data
US 2020/0030055 A1   Jan. 30, 2020

Related U.S. Application Data

(60) Provisional application No. 62/702,943, filed on Jul. 25, 2018, provisional application No. 62/702,946, (Continued)

(51) Int. Cl.
*F16M 11/02*  (2006.01)
*A61B 90/50*  (2016.01)
(Continued)

(52) U.S. Cl.
CPC .............. *A61B 90/50* (2016.02); *F16D 65/14* (2013.01); *F16M 11/2014* (2013.01); *A61B 2090/508* (2016.02); *F16D 2121/14* (2013.01)

(58) Field of Classification Search
CPC ... A61B 2090/508; A61B 90/35; F16D 49/16; F16D 65/065; F16M 2200/022
See application file for complete search history.

(56) References Cited

U.S. PATENT DOCUMENTS 875,019 A   7/1907   Wahlert
957,492 A   5/1910   Brown
(Continued)

FOREIGN PATENT DOCUMENTS

DE   102016005785 A1   11/2017
EP       1239805 A1    9/2002
(Continued)

OTHER PUBLICATIONS

International Search Report and Written Opinion for corresponding International Application PCT/US2019/042732 dated Sep. 30, 2019.
(Continued)

*Primary Examiner* — Bradley Duckworth
(74) *Attorney, Agent, or Firm* — Renner, Otto, Boisselle & Sklar, LLP

(57) ABSTRACT

A medical device support system including a central shaft; an extension arm; and a brake assembly. The extension arm has a support for a medical device and a hub at its proximal end mounted to the central shaft for pivotable movement about the central shaft. The brake assembly is secured in the hub for rotation therewith and includes first and second discrete arc shape clamp pieces that are detachably coupled to one another at one end for flexural movement relative to a coupling joint and that are free at an opposite end. The brake assembly includes an actuator configured to flex the first and second clamp pieces relative to the coupling joint toward and away from each other to respectively increase and decrease a frictional braking force to the central shaft.

22 Claims, 10 Drawing Sheets

Related U.S. Application Data filed on Jul. 25, 2018, provisional application No. 62/702,947, filed on Jul. 25, 2018, provisional application No. 62/702,948, filed on Jul. 25, 2018, provisional application No. 62/799,096, filed on Jan. 31, 2019, provisional application No. 62/799,100, filed on Jan. 31, 2019, provisional application No. 62/799,113, filed on Jan. 31, 2019, provisional application No. 62/799,202, filed on Jan. 31, 2019, provisional application No. 62/809,173, filed on Feb. 22, 2019, provisional application No. 62/825,078, filed on Mar. 28, 2019, provisional application No. 62/828,090, filed on Apr. 2, 2019.

(51) Int. Cl.
*F16M 11/20* (2006.01)
*F16D 65/14* (2006.01)
*F16D 121/14* (2012.01)

(56) References Cited

U.S. PATENT DOCUMENTS

| | | | | |
|---|---|---|---|---|
| 3,866,722 A * | 2/1975 | Kjos | ............... | F16D 49/16 |
| | | | | 188/75 |
| 4,200,407 A * | 4/1980 | Bianco | ............... | B21B 31/07 |
| | | | | 403/261 |
| 4,889,211 A * | 12/1989 | Carlson | ............... | B41F 13/02 |
| | | | | 188/68 |
| 5,090,522 A * | 2/1992 | Korff | ............... | E05F 5/00 |
| | | | | 188/166 |
| 6,142,264 A * | 11/2000 | Lin | ............... | F16D 49/16 |
| | | | | 188/20 |
| 6,464,268 B1 | 10/2002 | Hough et al. | | |
| 6,471,165 B2 * | 10/2002 | Twisselmann | ............... | F16M 11/18 |
| | | | | 248/123.11 |
| 6,872,023 B2 * | 3/2005 | Liao | ............... | F16C 11/103 |
| | | | | 403/110 |
| 7,849,978 B2 * | 12/2010 | Graham | ............... | A61G 7/0503 |
| | | | | 188/171 |
| 9,103,178 B2 * | 8/2015 | Beach | ............... | E21B 31/20 |
| 9,151,422 B2 | 10/2015 | Kayacik et al. | | |
| 9,706,843 B2 * | 7/2017 | Hung | ............... | F16M 11/105 |
| 10,335,961 B2 * | 7/2019 | Christiansen | ............... | A61B 34/70 |
| 10,591,006 B2 * | 3/2020 | Puterbaugh | ............... | F16D 49/16 |
| 2012/0137924 A1 * | 6/2012 | Boren | ............... | B66C 9/18 |
| | | | | 105/150 |
| 2017/0326738 A1 | 11/2017 | Christiansen et al. | | |

FOREIGN PATENT DOCUMENTS

| | | |
|---|---|---|
| FR | 1441338 A | 6/1966 |
| WO | 0145627 A1 | 6/2001 |

OTHER PUBLICATIONS

Cramik Enterprises Product Information; www.homedepot.com/p/Cramik-Enterprises-1-in Galvanize . . . .
Datasheet for The FastMount™; Holloway America.

\* cited by examiner

BRAKE ASSEMBLY FOR MEDICAL DEVICE SUPPORT SYSTEM

This application claims priority to U.S. Patent Application No. 62/702,943 filed Jul. 25, 2018; U.S. Patent Application No. 62/702,946 filed Jul. 25, 2018; U.S. Patent Application No. 62/702,947 filed Jul. 25, 2018; U.S. Patent Application No. 62/702,948 filed Jul. 25, 2018; U.S. Patent Application No. 62/799,096 filed Jan. 31, 2019; U.S. Patent Application No. 62/799,100 filed Jan. 31, 2019; U.S. Patent Application No. 62/799,113 filed Jan. 31, 2019; U.S. Patent Application No. 62/799,202 filed Jan. 31, 2019; U.S. Patent Application No. 62/809,173 filed Feb. 22, 2019; U.S. Patent Application No. 62/825,078 filed Mar. 28, 2019; and U.S. Patent Application No. 62/828,090 filed Apr. 2, 2019. These prior applications are incorporated herein by reference.

FIELD OF INVENTION

This application relates generally to a brake assembly for a medical device suspension system or carry system for use in, for example, a hospital examination room, a clinic, a surgery room or an emergency room, and more particularly to a brake assembly that has a multi-piece structure that simplifies assembly and field service.

BACKGROUND

Medical device suspension systems or carry systems are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. The supports typically include a central shaft or support column that is suspended from the ceiling or mounted to a wall, and one or more generally horizontal extension arms mounted for rotational movement about the shaft. A frictional brake is provided near the pivot location of the extension arm that is operable to maintain the extension arm in the desired angular position and to permit angular adjustment by a suitable force against the extension arm. The extension arm can be rotatably adjusted about the column to a desired angular position to provide appropriate access to medical devices and components associated with the arm.

Most of the current support systems utilize mechanical radial braking devices to provide the required rotational performances of system components. The basic principle of these devices is that the force needed to achieve the desired level of frictional braking is applied in the radial direction, transverse or perpendicular to the axis of component rotation. One example is a clamp assembly that has a generally C-shape construction. The clamp assembly is installed over the central shaft and into a hub portion of the pivoting extension arm. An actuator, which may also be part of the hub, is used to urge opposite sides of the brake clamp toward and away from the shaft. This process creates a normal force between the brake clamp and the shaft, and provides necessary frictional force to control the pivotable movement of the arm around the shaft.

For some medical device suspension systems or carry systems, there remain various shortcomings, drawbacks, and disadvantages relative to certain applications. For example, the C-shape clamp assembly has a split ring structure that can only be installed by positioning the split ring at an upper end (or lower end) of the support shaft and sliding the ring to the appropriate axial position along the shaft, i.e. near the pivoting location of the extension arm. This typically is done in a factory prior to shipping and installing the system in a surgery room or clinic, since the brake assembly must already be located on the shaft prior to mounting the shaft to a support surface or prior to attaching the extension arm to the shaft. Servicing the brake assembly also can be problematic, since the support system must be disassembled to provide access to an upper or lower shaft end. This usually requires removal and transport of the system from its health treatment room to an appropriate service facility. The brake assembly of these medical device support systems therefore is not easily field replaceable/serviceable.

Accordingly, there remains a need for further contributions in this area of technology.

SUMMARY OF INVENTION

The application relates to a multi-piece brake assembly for a medical device support system, in which the brake assembly has first and second discrete arc shape clamp pieces that can be easily assembled to, and removed from, a central shaft of the support system, and therefore simplifies and adds efficiency to the factory assembly and field service of the medical device support system.

According to one aspect of the invention, a medical device support system includes a central shaft; an extension arm having a support for a medical device and a hub at its proximal end mounted to the central shaft for pivotable movement about the central shaft; and, a brake assembly secured in the hub for rotation therewith and including first and second discrete arc shape clamp pieces that are detachably coupled to one another at one end for flexural movement relative to a coupling joint and that are free at an opposite end. The brake assembly includes an actuator configured to flex the first and second clamp pieces relative to the coupling joint toward and away from each other to respectively increase and decrease a frictional braking force to the central shaft.

Embodiments of the invention may include one or more of the following additional features separately or in combination.

The first and second arc shape clamp pieces may form a multi-piece split collar around the central shaft that is configured to contract and expand relative to the central shaft in response to flexural movement of the first and second arc shape clamp pieces relative to the coupling joint.

When the first and second clamp pieces are flexed toward each other to increase the frictional braking force to the central shaft, the first and second clamp pieces may have an arc shape contact with the outer periphery of the central shaft.

The brake assembly may be configured to operate in a passive manner, preventing motion of the extension arm relative to the central shaft by means of the frictional braking force, wherein the frictional braking force can be overcome by a user pushing on the extension arm.

The first and second arc shape clamp pieces may be diametrically opposed from one another on opposite sides of the central shaft.

The medical device may be a surgical light.

The first and second arc shape clamp pieces may include respective liners made of a material selected from polyolefins, polyesters, acetals, polyamides, fluorinated polymers, vinyls, acrylics, polycarbonates, polyimides, polysulphones, and blends and alloys thereof.

The first and second arc shape clamp pieces may include unreinforced, semi-crystalline thermoplastic polyester based on polyethylene terephthalate (PET-P).

The first and second arc shape clamp pieces include respective first and second polymer liners made of UHMW-PE.

According to another aspect of the invention, a brake assembly for a medical device support system having a central shaft, includes first and second discrete arc shape clamp pieces that are detachably coupled to one another at one end for flexural movement relative to a coupling joint and that are free at an opposite end. The first and second arc shape clamp pieces are configured to flex relative to the coupling joint toward and away from each other to respectively increase and decrease a frictional braking force to the central shaft.

Embodiments of the invention may include one or more of the following additional features separately or in combination.

The first and second arc shape clamp pieces may form a multi-piece split collar around the central shaft that is configured to contract and expand relative to the central shaft in response to flexural movement of the first and second arc shape clamp pieces relative to the coupling joint.

The first and second arc shape clamp pieces may be detachably coupled to one another by being interlocked to each other at the one end.

The one ends of the first and second arc shape clamp pieces may include respective first and second axially extending protrusions that circumferentially abut one another to resist flexural movement of the first and second arc shape clamp pieces toward each other relative to the coupling joint.

The one ends of the first and second arc shape clamp pieces may have respective first and second axially extending tabs and first and second axially extending notches, and the first axially extending tab may fit within the second axially extending notch and the second axially extending tab may fit within the first axially extending notch.

The one ends of the first and second arc shape clamp pieces may be slidable axially and radially relative to one another.

The first and second arc shape clamp pieces may be detachably coupled to one another by a hinge at the one end.

The first and second arc shape clamp pieces may have an identical geometry.

According to another aspect of the invention, there is provided a method of installing a brake assembly in a medical device support system having a central shaft, the method including providing first and second discrete arc shape clamp pieces of the brake assembly at one side of a central shaft; moving either the connecting ends or the free ends around the central shaft to an opposite side of the central shaft so that the connecting ends and free ends are situated at opposite sides of the central shaft; coupling the connecting ends of the first and second arc shape clamp pieces together for flexural movement relative to a coupling joint at the connecting ends and for free movement at the free ends; arranging the first and second arc shape clamp pieces relative to the central shaft to respectively increase and decrease a frictional braking force to the central shaft in response to flexural movement of the first and second arc shape clamp pieces relative to the coupling joint; and, securing the brake assembly in a hub of an extension arm for rotation with the extension arm about the central shaft.

Embodiments of the invention may include one or more of the following additional features separately or in combination.

The arranging may include arranging the first and second arc shape clamp pieces to form a multi-piece split collar around the central shaft that is configured to contract and expand relative to the central shaft in response to flexural movement of the first and second arc shape clamp pieces relative to the coupling joint.

The coupling may include interlocking the connecting ends of the first and second arc shape clamp pieces.

The coupling may include sliding axially the first and second arc shape clamp pieces relative to one another.

The coupling may include hingedly connecting the connecting ends of the first and second arc shape clamp pieces.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

DETAILED DESCRIPTION

Figure 1:
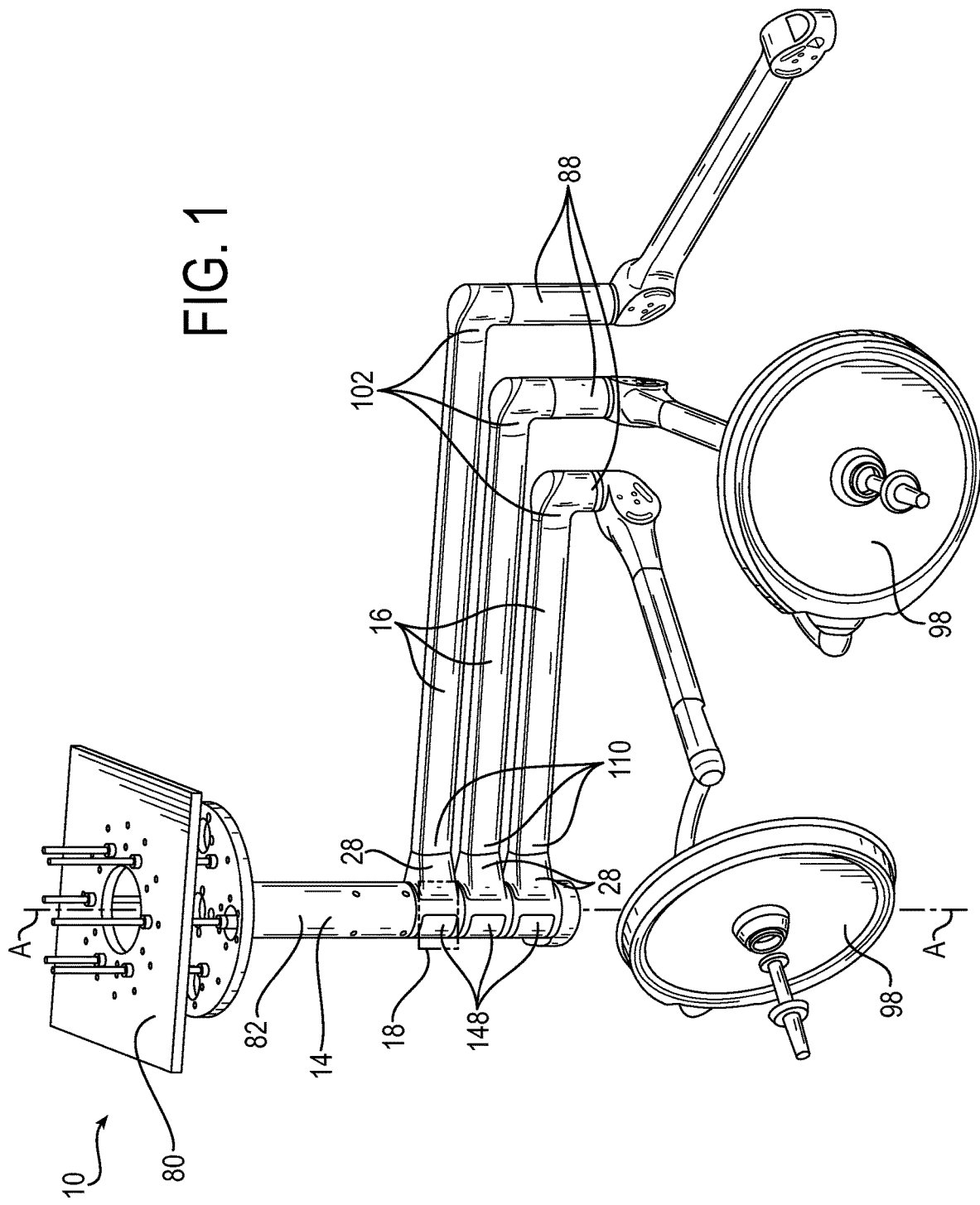
FIG. 1 is a perspective view of a medical device support system in accordance with an embodiment of the invention.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

Figure 2:
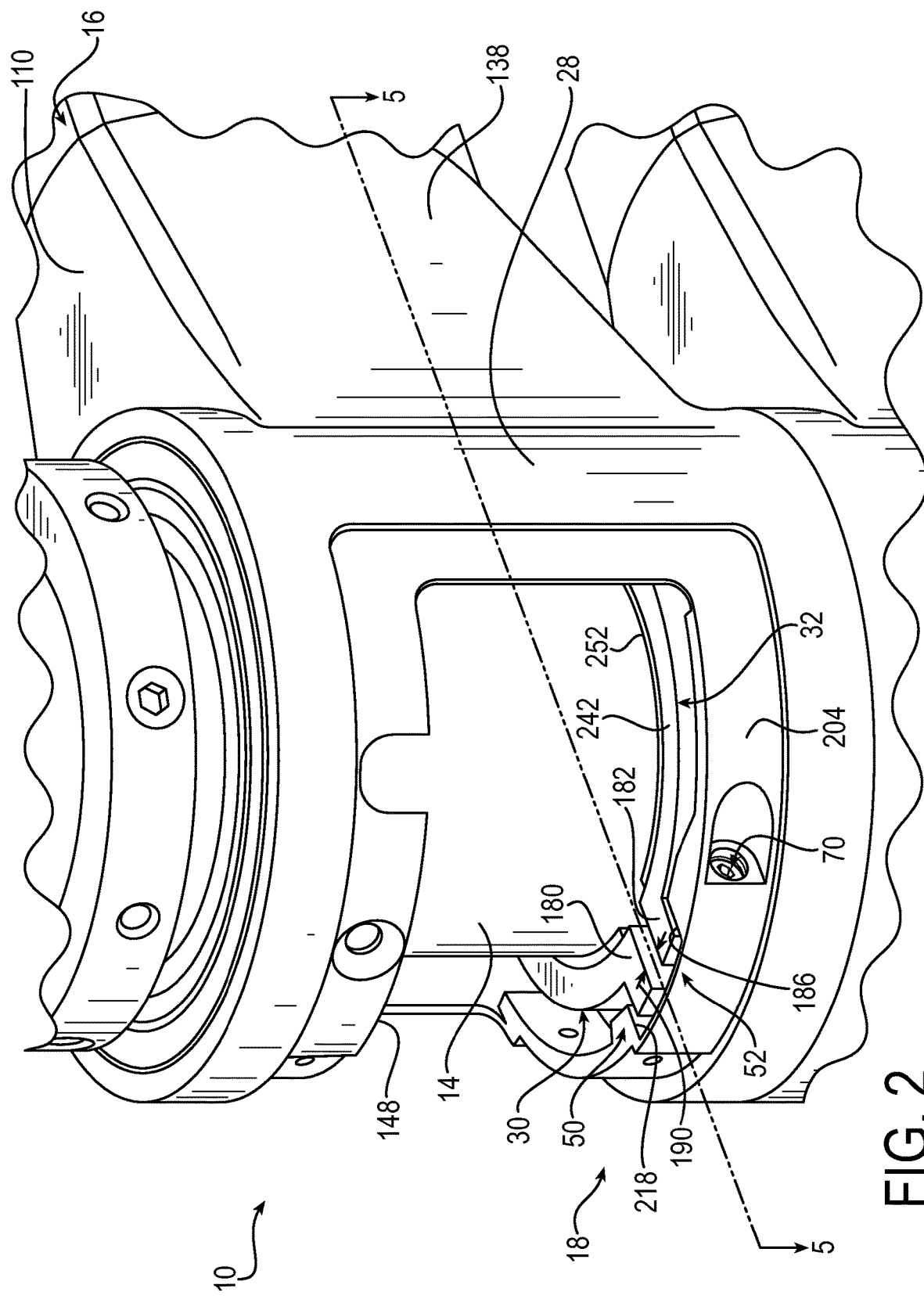
FIG. 2 is a perspective view of a portion of the medical device support system of FIG. 1, showing a pivot location of an extension arm of the system.
Figure 3:
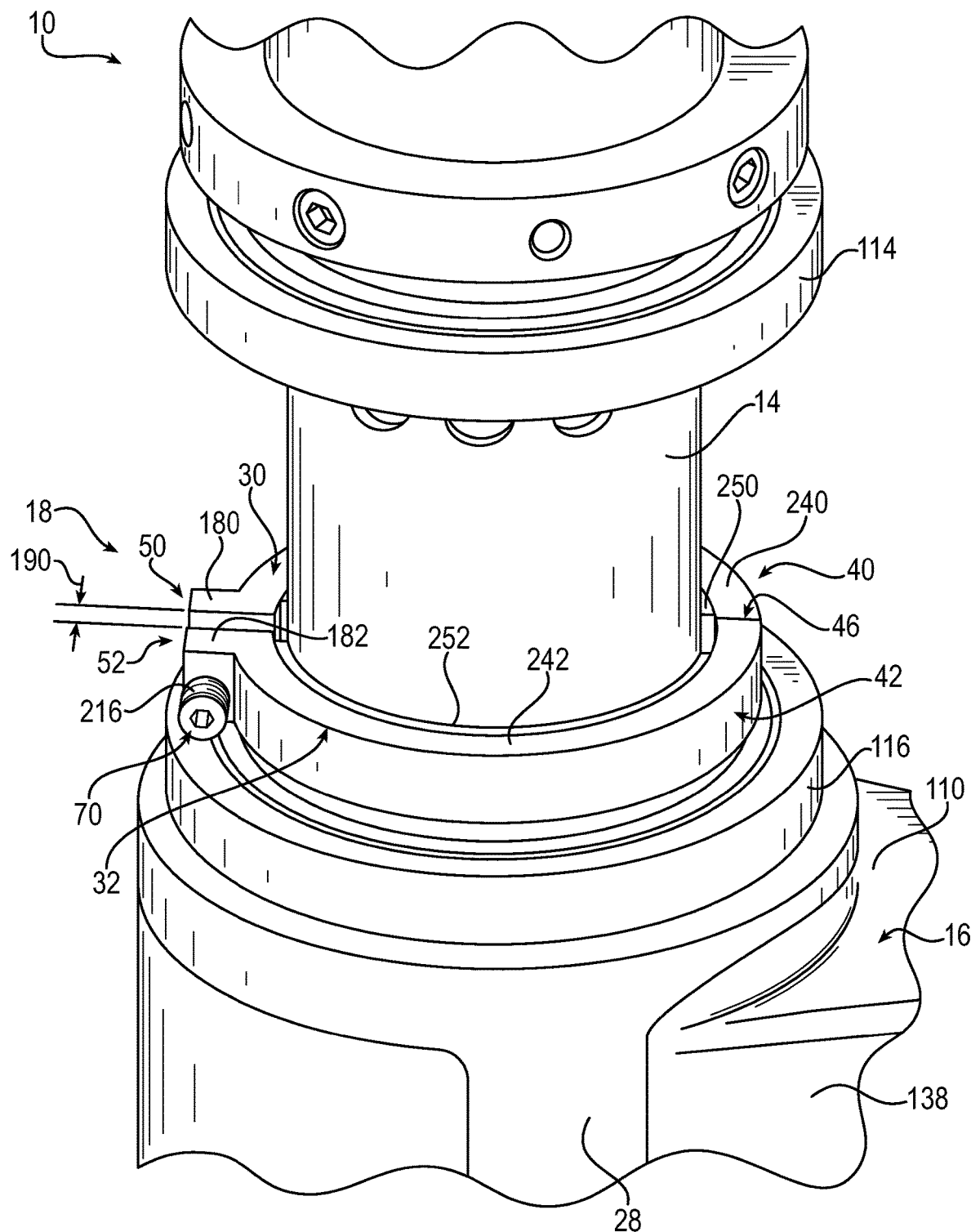
FIG. 3 is a perspective view of a portion of the medical device support system of FIG. 1, showing a pivot location of an extension arm of the system with portions of the extension arm removed to show inner detail.
Figure 4:
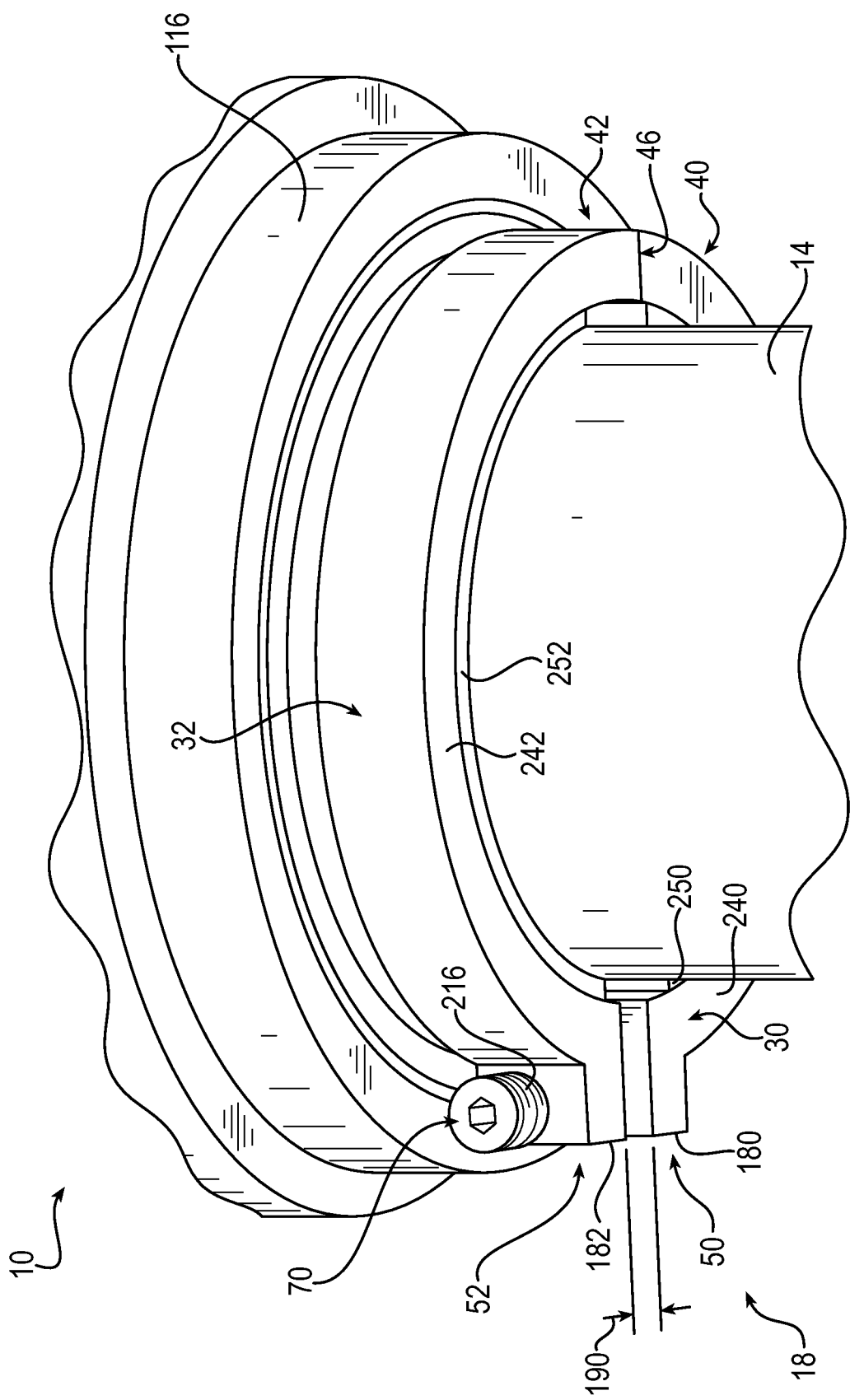
FIG. 4 is a perspective view of a portion of the medical device support system of FIG. 1, showing a pivot location of an extension arm of the system with portions of the extension arm removed to show inner detail.
Figure 5:
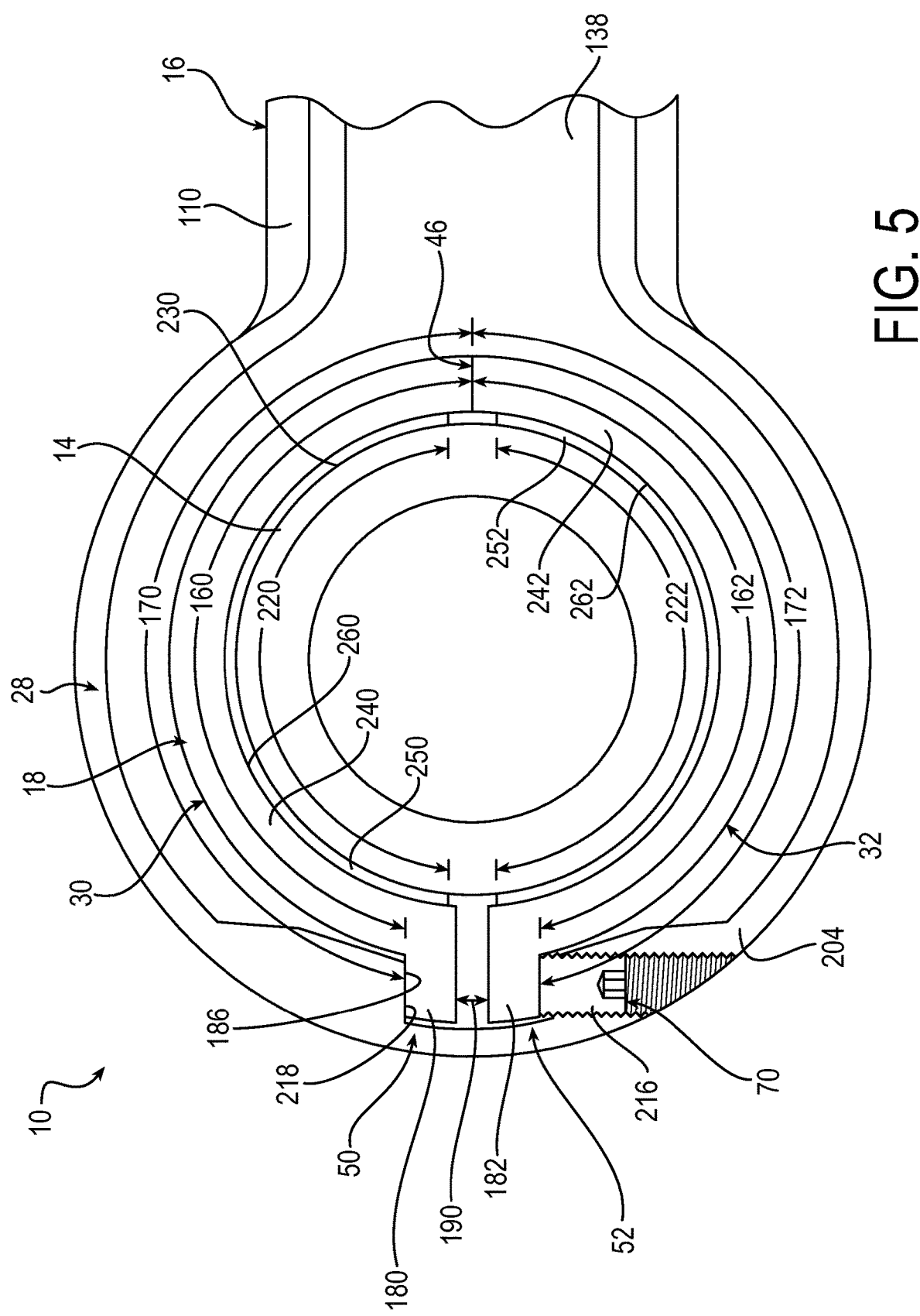
FIG. 5 is a cross-section view of the medical device support system of FIG. 1, as viewed from the plane 5-5 in FIG. 2.

FIGS. 1-5 show a medical device support system 10 that includes a central shaft 14, at least one extension arm 16 rotatably mounted to the shaft 14, and a brake assembly 18 secured in a hub 28 of the extension arm 16 for rotation with the extension arm 16. As shown in FIGS. 4 and 5, the brake assembly 18 includes first and second discrete arc shape clamp pieces 30, 32 that are detachably coupled to one another at one end 40, 42 for flexural movement relative to a coupling joint 46 while being free to move at an opposite end 50, 52. An actuator 70 is configured to flex the first and second clamp pieces 30, 32 relative to the coupling joint 46 toward and away from each other to respectively increase and decrease a frictional braking force to the central shaft 14. As will be described in greater detail below, the multi-piece structure of the brake assembly 18 enables the first and second arc shape clamp pieces 30, 32 to be easily assembled to, and removed from, the central shaft 14, and therefore simplifies and adds efficiency to the factory assembly and field service of the medical device support system 10.

Referring to FIG. 1, the illustrative medical device support system 10 is a suspension type carrying support system for use in a hospital examination room, a clinic, a surgery room, an emergency room, among others. The central shaft 14 extends along an axis A-A. The central shaft 14 may be fixed to a ceiling support 80 to remain stationary relative to the ceiling. It will be appreciated, of course, that the medical device support system 10 may have any suitable suspension or carrying structure and that the central shaft 14 may be attached to a ceiling, wall, floor, movable cart, or a combination of the foregoing. The central shaft 14 of the medical device support system 10 has a circular shape in axial cross section and extends vertically downward from the ceiling support 80. A column section 82 surrounds an upper portion of the central shaft 14 and houses upper portions of accessory and service lines such as power cables for surgical lights and other power requirements, control wiring for control electronics, and/or tubing for irrigation, suction, etc. A plurality of extension arms 16, three in the illustrative embodiment, are mounted for rotatable movement to the central shaft 14 and extend laterally outward from the central shaft 14. In the FIG. 1 embodiment, the extension arms 16 extend horizontally, or perpendicularly, relative to the central shaft 14.

Each extension arm 16 is equipped with a support 88 for a medical device 98. The illustrative support 88 is a vertical column 88 extending downward from a distal end 102 of the horizontal extension arm 16. The vertical column 88 may be mounted for rotatable movement to the distal end 102 of the extension arm 16 by means of a bearing, and may be equipped to frictionally engage the distal end 102, for example, by means of a brake assembly 18 in the same manner that the extension arm 16 is rotatably mounted and braked relative to the central shaft 14. In the FIG. 1 embodiment, the medical device 98 comprises a surgical light 98 attached to a bottom end of the vertical column 88. Of course, the medical device support system 10 need not be limited as such and other embodiments are contemplated. For example, the medical device 98 may comprise a patient monitor, a supply console, a camera detector head, a medical instrument, a ventilator system, a suction device, among others. A control console, if provided, may provide controls for navigation of a medical instrument that is either coupled to or remote from the extension arm 16.

The hub 28 is located at the proximal end 110 of the extension arm 16 and is mounted to the central shaft 14 for pivotable movement about the central shaft 14. In the illustrative embodiment, each hub 28 includes upper and lower bearing mounts 114, 116, shown in FIG. 3, that house respective upper and lower pivot bearings mounted to the central shaft 14. Any suitable pivot bearings may be used to facilitate the relative rotational movement between the extension arm 16 and the central shaft 14, including for example ball bearings, sleeve bearings, bushings, rotary joints and/or swivel joints. Each hub 28 provides passages for routing accessory and service lines from the upper column section 82 to the radial extent 138 of the extension arm 16 and/or vice versa. Each hub 28 is also provided with an access opening 148 to enable access to the central shaft 14, the brake assembly 18, and the accessory and service lines.

Reference is now made to FIGS. 2-9 which show greater detail of the brake assembly 18. The brake assembly 18 is secured in the hub 28 for rotation with the hub 28. As shown in FIGS. 4 and 5, the brake assembly 18 includes first and second discrete arc shape clamp pieces 30, 32 that are detachably coupled to one another at one end 40, 42 for flexural movement relative to a coupling joint 46 while being free to move at an opposite end 50, 52. In the illustrative embodiment, each of the first and second discrete arc shape clamp pieces 30, 32 of the brake assembly 18 has a circumferential portion 160, 162, a connecting end 40, 42 at one end of the circumferential portion 160, 162, and a free end 50, 52 at an opposite end of the circumferential portion 160, 162. As shown in FIG. 5, the arc shape clamp pieces 30, 32 in their assembled state form a multi-piece split collar or ring wherein the circumferential portions 160, 162 form the ring portion thereof, an interface between the connecting ends 40, 42 forms a first split thereof, and a gap between the free ends 50, 52 forms a second split thereof. The circumferential portions 160, 162 are sized to fit within and radially inward of inner circumferential portions 170, 172 of the hub 28. As shown in FIG. 3, the arc shape clamp pieces 30, 32 may rest by means of gravity directly on the lower bearing mount 116. A retaining snap ring may be mounted in a groove in the central shaft 14 immediately above, or a slight clearance above, the arc shape clamp pieces 30, 32 and/or immediately below, or a slight clearance below, the arc shape clamp pieces 30, 32 to axially retain or guide the arc shape clamp pieces 30, 32 relative to the central shaft 14.

The free ends 50, 52 of the arc shape clamp pieces 30, 32 include tabs 180, 182 that protrude radially outwardly relative to the circumferential portions 160, 162. As shown in FIGS. 2 and 5, the radially protruding tabs 180, 182 fit within a radially protruding notch 186 in the hub 28, which notch 186 is disposed circumferentially between the inner circumferential portions 170, 172 of the hub 28. The tabs 180, 182, when installed in the hub notch 186, circumferentally oppose one another and form a circumferential gap therebetween referred to herein as a deflection compensation split 190.

The brake assembly 18 further includes an actuator 70 that is housed in a wall portion 204 of the hub 28, as shown in FIGS. 2 and 5. The actuator 70 is operative selectively to apply a compressive force to the tabs 180, 182 to urge the first and second arc shape clamp pieces 30, 32 toward one another thereby to impart a frictional braking force to the central shaft 14. In the illustrative embodiment, the actuator 70 comprises a set screw 216 although any type of actuator 70 may be employed that is operative to urge the first and second arc shape clamp pieces 30, 32 toward one another. The set screw 216 is configured to apply a load to the rear of the tab 182. The set screw 216 is threaded into the wall portion 204 of the hub 28 and when threaded inward compresses the tab 182 toward the opposite tab 180. The opposite tab 180 provides resistance to the compressive force applied by the set screw 216 by resting against a wall 218 of the notch 186 in the hub 28.

In operation, tightening the set screw 216 compresses the tabs 180, 182 and thereby narrows the deflection compensation split 190 and flexes the first and second arc shape clamp pieces 30, 32 toward one another relative to the coupling joint 46. Loosening the set screw 216 causes the tabs 180, 182 to separate from one another owing to the resistive force imparted by the notch wall 218 of the hub 28 against the rear of the tab 180, which results in the deflection compensation split 190 expanding and the first and second arc shape clamp pieces 30, 32 unflexing away from one another relative to the coupling joint 46. Thus, the deflection compensation split 190 between the free ends 50, 52 compensates for deflection caused by the application of compressive force on the tabs 180, 182, which creates a tangential frictional force that supplies the braking relative to the central shaft 14. The set screw 216, or actuator 70, is configured to increase and decrease the frictional braking force applied by the brake assembly 18 to the central shaft 14 to respectively increase and decrease the resistance to pivotable movement of the extension arm 16 about the central shaft 14. The actuator 70 and brake assembly 18 are configured to operate in a passive manner, preventing motion of the extension arm 16 relative to the central shaft 14 by means of an "always-on" frictional braking force that can be overcome by a user pushing on the extension arm 16. The amount of frictional resistance can be adjusted as desired by the user by adjusting the actuator 70. The actuator 70 can be used to adjust the frictional resistance as suited for a particular physician and/or on a periodic basis to ensure the previously set frictional resistance still is in place and not loosened over time.

It will be appreciated that a suitable actuator can be employed to generate a lock mode, a frictional resistance mode, and/or a release mode. For example, the actuator can be configured to adjust the brake assembly 18 to generate a braking force, whether by friction or an interengaging mechanism such as a cam lock or piston lock, sufficient to lock the extension arm 16 to the central shaft 14, and/or to generate a frictional braking force that prevents rotation of the extension arm 16 about the central shaft 14 yet enables a user to overcome the resistance by pushing the extension arm 16 about the central shaft 14, and/or to generate a relatively lower or zero frictional braking force sufficient to free or release the extension arm 16 for pivotable movement about the central shaft 14 with relatively less or negligible force by the user. It will further be appreciated that the brake assembly 18 could be adapted for an active braking system, one which provides an active braking functionality that can apply a frictional braking force actively, for example, by means of electromagnetic actuation, pneumatic actuation, or hydraulic actuation.

The multi-piece split collar that is formed by the first and second arc shape clamp pieces 30, 32 is disposed around the central shaft 14 and is configured to contract and expand relative to the central shaft 14 in response to the flexural movement of the first and second arc shape clamp pieces 30, 32 relative to the coupling joint 46. As will be appreciated, as the first and second arc shape clamp pieces 30, 32 of the brake assembly 18 are flexed relative to the coupling joint 46, the circumferential portions 160, 162 and free ends 50, 52 of the arc shape clamp pieces 30, 32 move closer together and farther apart to respectively contract and expand the split collar. As shown in FIG. 5, when the first and second clamp pieces 30, 32 are flexed toward each other to increase the frictional braking force applied to the central shaft 14, the first and second clamp pieces 30, 32 each have an angular range or arc shape contact 220, 222 with the outer periphery 230 of the central shaft 14 of about 165 degrees, or a total of about 330 degrees. Of course, the multi-piece split collar may be formed by more than two discrete arc shape clamp pieces, for example, three or four arc shape clamp pieces, with circumferentially adjacent pieces being detachably coupled together. Further, although the illustrative first and second arc shape clamp pieces 30, 32 are diametrically opposed from one another on opposite sides of the central shaft 14, it will be appreciated that the arc shape clamp pieces 30, 32 may be other than diametrically opposed, for example, where there are more than two arc shape clamp pieces provided. For example, four arc shape clamp pieces may be equally circumferentially disposed about the central shaft 14; that is, each piece may be 90 degrees apart from an adjacent piece.

Figure 6:
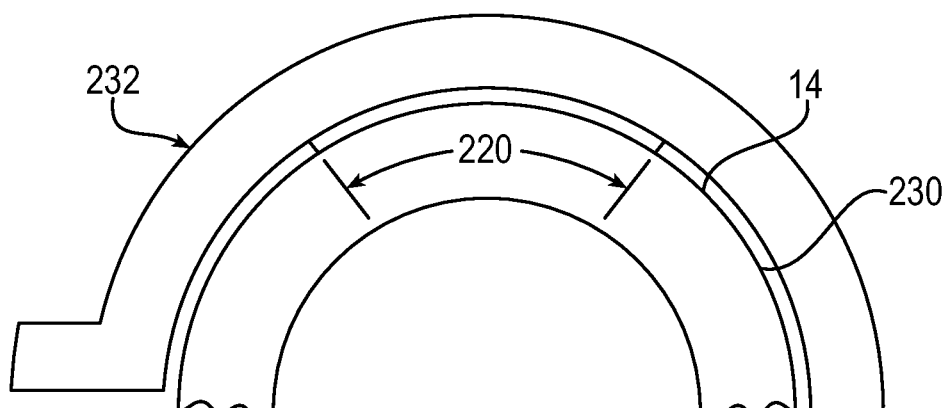
FIG. 6 is a top view of view an arc shape clamp piece of a brake assembly in accordance with an embodiment of the invention.
Figure 7:
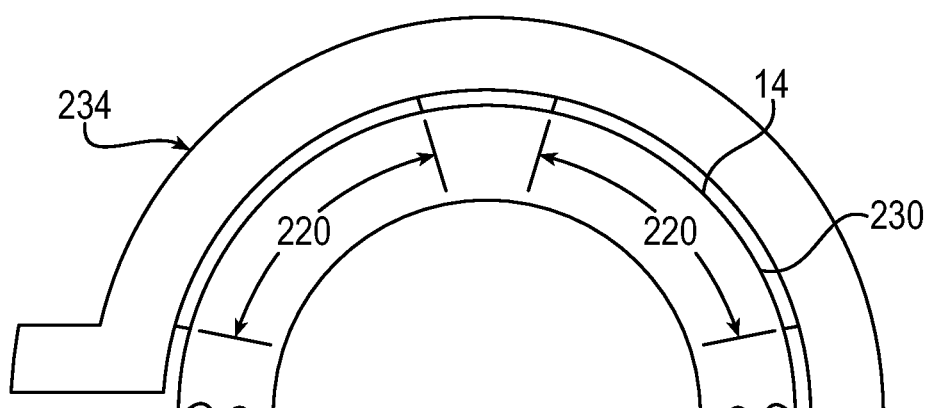
FIG. 7 is a top view of view an arc shape clamp piece of a brake assembly in accordance with another embodiment of the invention.
Figure 8:
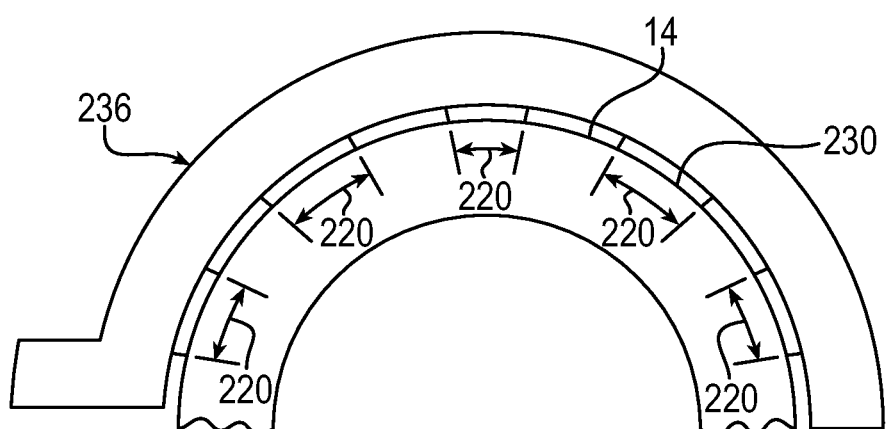
FIG. 8 is a top view of view an arc shape clamp piece of a brake assembly in accordance with another embodiment of the invention.

It will also appreciated that the angular range contact of the arc shape clamp pieces may be other than 165 degrees, and thus other than a total of 330 degrees. For example, FIG. 6 shows an alternate embodiment of an arc shape clamp piece 232 for which the angular range contact with the central shaft 14 is about 30 degrees, thus totaling a 60 degree angular range contact in the case where opposing arc shape clamp pieces 232 have identical geometries. FIG. 7 shows another embodiment in which the arc shape clamp piece 234 has two angular range contacts, one each of about 30 degrees, thus totaling a 120 degree angular range contact in the case where opposing arc shape clamp pieces 234 have identical geometries. FIG. 8 shows yet another embodiment of an arc shape clamp piece 236. Here, the arc shape clamp piece 236 has five angular range contacts, one each of about 15 degrees, thus totaling a 150 degree angular range contact in the case where opposing arc shape clamp pieces 236 have identical geometries. Still other embodiments may have other angular range contacts. It will be understood that opposing arc shape clamp pieces need not have the same angular range contacts, whether in the quantity or size of the arc shape clamp pieces, or the components that form the arc shape clamp pieces.

Figure 9:
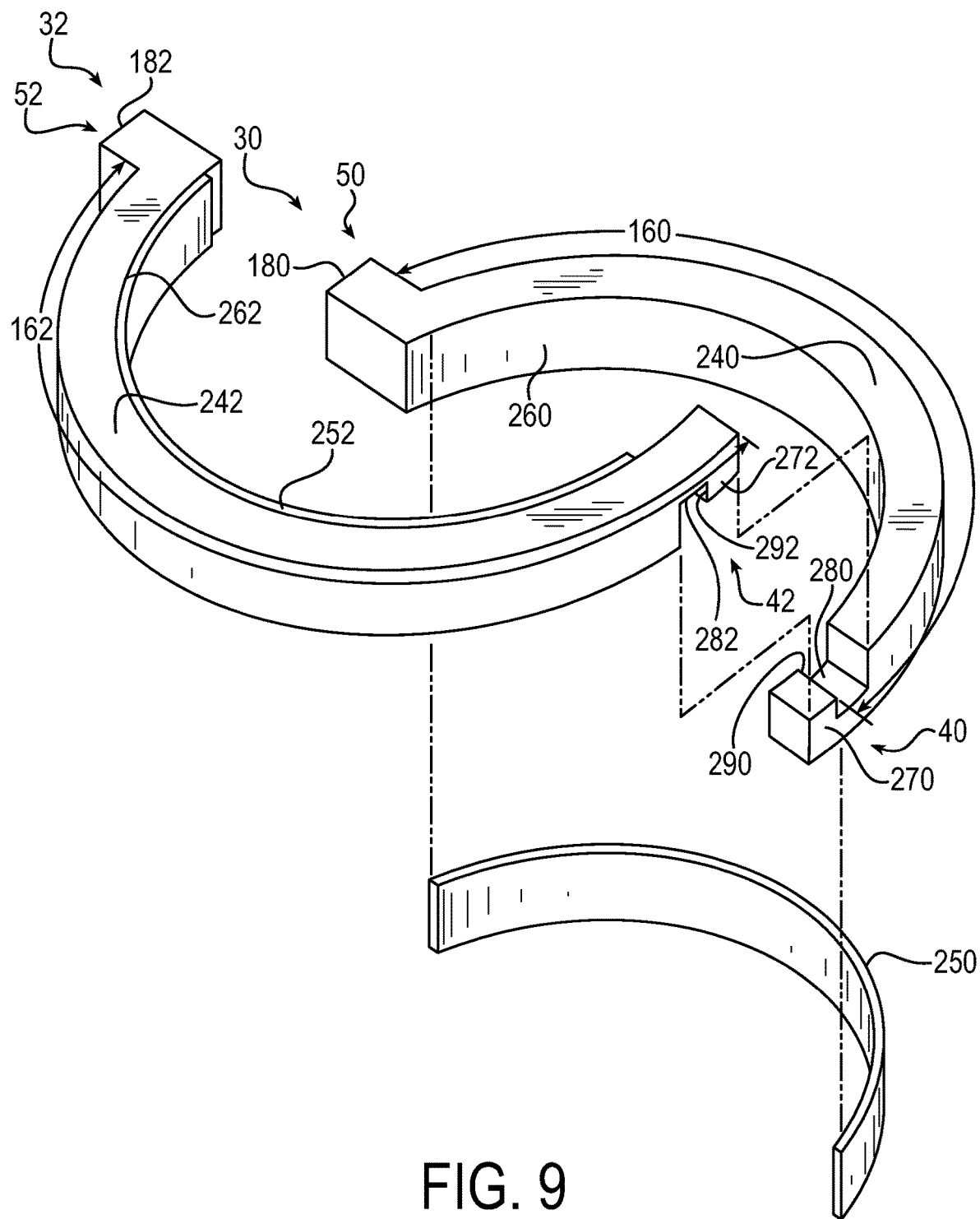
FIG. 9 is an exploded perspective view of first and second arc shape clamp pieces of a brake assembly in accordance with an embodiment of the invention.
Figure 10:
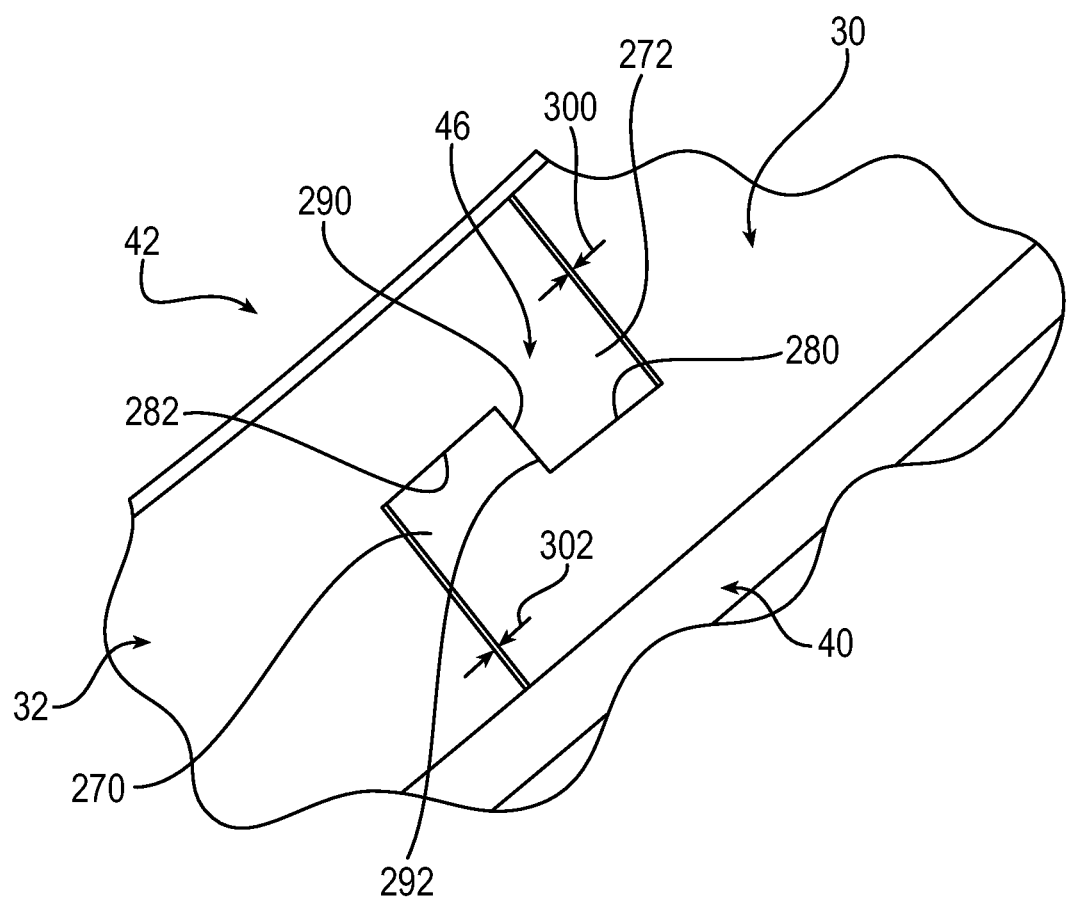
FIG. 10 is a partial side view of a coupling joint of the first and second arc shape clamp pieces of the brake assembly of FIG. 9, showing connecting ends of the pieces detachably coupled to one another.

FIGS. 9 and 10 show greater details of the first and second arc shape clamp pieces 30, 32. The first and second arc shape clamp pieces 30, 32 include an arc shape backing piece 240, 242 and a polymer liner 250, 252 mounted to a radially inner wall 260, 262 of the arc shape backing piece 240, 242, for example by adhesive bonding. In the illustrative embodiment, the arc shape clamp pieces 30, 32 have identical geometries, wherein the arc shape backing pieces 240, 242 have a one part geometry and the polymer liners 250, 252 have a one part geometry. The identical geometries eliminate the need for extra unique component designs. It will be appreciated that the arc shape clamp pieces 30, 32 may have different geometries, or components thereof may have some identical geometries and some different geometries.

The arc shape backing pieces 240, 242 may be made of any suitable materials, for example, metal or metal alloy. The arc shape backing pieces 240, 242 may be made by means of casting, machining, powdered metallurgy and/or metal injection molding. In some applications, the arc shape backing pieces 240, 242 may be made by means of additive manufacturing.

The liners may be formed from any suitable thermoset polymer or thermoplastic polymer. The polymer material may have a low to medium coefficient of friction of about 0.12 to about 0.27, a wear factor no less than about 1.20 E-14 m2/N, a tensile strength of about 4400 to about 12400 psi, a coefficient of linear thermal expansion of about 3.3 to about 7.2 $10^{\wedge}$-5/F, and a water absorption (50% RH) in a range of about 0.07% to about 0.22%. As one example, the liners may be formed from an unreinforced, semi-crystalline thermoplastic polyester based on polyethylene terephthalate (PET-P), for example, ERTALYTE®. As another example, the liners may be formed from a compression molded ultra high molecular weight polyethylene (UHMW-PE), or an extruded UHMW-PE. As another example, the liners may be formed from an injection molded acetal homopolymer, for example Delrin® 100P. Other suitable polymeric materials include polyolefins (for example, HDPE, LDPE, polypropylene), polyesters (for example, PET, PBT), acetals (for example, Delrin), polyamides (for example, Nylon), fluorinated polymers (for example, PTFE, PFA, FEP, PVDF, ETFE), vinyls (for example, PVC), acrylics (for example, PMMA), polycarbonates, polyimides (for example, PEI), polysulphones (for example, PES), among others, and blends and alloys thereof. The liners may be made by means of injection molding, machining, compression molding and/or extruding. In some applications, the liners may be made by means of additive manufacturing.

The first and second arc shape clamp pieces 30, 32 of the embodiment shown in FIGS. 9 and 10 are detachably coupled to one another by being interlocked to each other at their respective connecting ends 40, 42. As shown in FIG. 10, the connecting ends 40, 42 have respective first and second axially extending tabs 270, 272 and first and second axially extending notches 280, 282, and are configured to be slidable axially and radially relative to one another. The interlocking split allows the first and second clamp pieces 30, 32 to interlock when the compressive loads applied to the tabs 180, 182 create tensile loads at the opposite end connecting ends 40,42 of the clamp split collar. The arc shape clamp pieces 30, 32 are coupled together by fitting or inserting the first axially extending tab 270 within the second axially extending notch 282, and by fitting or axially inserting the second axially extending tab 272 within the first axially extending notch 280. Once coupled together, the connecting ends 40, 42 form the coupling joint 46 that functions as the joint relative to which the arc shape clamp pieces 30, 32 flex.

During application of a frictional braking force to the central shaft 14, the axially extending tabs 270, 272 circumferentially abut one another at respective opposite facing walls 290, 292 to resist flexural movement of the first and second arc shape clamp pieces 30, 32 toward each other relative to the coupling joint 46. The greater the frictional braking force, the greater is the circumferentially abutting resistance load applied by one facing wall 290 against the opposing facing wall 292.

As shown in FIG. 10, the axially extending notches 280, 282 have an angular width that is wider than the angular width of the axially extending tabs 270, 272. This provides an angular clearance 300, 302 between the tabs 270, 272 and the walls of the notches 280, 282 to facilitate fitting or insertion of the tabs 270, 272 within the respective notches 280, 282, and thus easy assembly of the interlocking split that forms the coupling joint 46. The radially protruding tabs 180, 182 are then positioned in the hub notch 186. In one form, in the initial assembly of the interlocking split and insertion of the tabs 180, 182 in the hub notch 186, the axially extending tabs 270, 272 may be circumferentially separate from one another such that the arc shape clamp pieces 30, 32 are in an unflexed or relaxed state. In another form, in the initial assembly of the interlocking split and insertion of the tabs 180, 182 in the hub notch 186, the axially extending tabs 270, 272 may be in circumferentially abutting relation at the opposite facing walls 290, 292 such that the arc shape clamp pieces 30, 32 are in a slightly flexed state. In any event, the actuator 70 may then be used to urge the first and second arc shape clamp pieces 30, 32 toward one another thereby to impart the desired frictional braking force to the central shaft 14. When the first and second arc shape clamp pieces 30, 32 are urged toward each other to apply the frictional braking force to the central shaft 14, the axially extending tabs 270, 272 and thus the arc shape clamp pieces 30, 32 engage one another and form the coupling joint 46 relative to which the arc shape clamp pieces 30, 32 flex in applying the frictional braking force to the shaft 14, as above described. Similarly, when the actuator 70 is backed off, the first and second arc shape clamp pieces 30, 32 flex away from each other to decrease the frictional braking force applied to the central shaft 14.

FIG. 9 shows the axially extending notches 280, 282 are open at their radially opposite ends. This enables radial movement of the axially extending tabs 270, 272 such that when the first and second arc shape clamp pieces 30, 32 are urged toward each other to apply a frictional braking force to the central shaft 14, the axially extending tabs 270, 272 and thus the arc shape clamp pieces 30, 32 shift radially relative to one another and, being in circumferentially abutting relation, engage one another and form the coupling joint 46 relative to which the arc shape clamp pieces 30, 32 flex in applying the frictional braking force to the shaft 14, as above described. Similarly, when the first and second arc shape clamp pieces 30, 32 are flexed away from each other to decrease the frictional braking force applied to the central shaft 14, the axially extending tabs 270, 272 and thus the arc shape clamp pieces 30, 32 move radially relative to one another as they unflex.

As will be appreciated, the first and second arc shape clamp pieces 30, 32 can "float" relative to each other axially, circumferentially, and radially. As such, when the actuator 70 urges the radially protruding tabs 180, 182 together to urge the arc shape clamp pieces 30, 32 closer together or opens the deflection compensation split 190 to allow the arc shape claim pieces 30, 32 to move apart, the arc shape clamp pieces 30, 32 are able to shift to a position that is most centered and aligned with respect to the central shaft 14. Thus, the floating capability enables the multi-piece split collar that is formed by the arc shape clamp pieces 30, 32 to be self-centering and self-aligning relative to the central shaft 14. This also allows for a built-in concentricity clearance between the hub 28 and the brake assembly 18, particularly over repeated angular adjustments of the extension arm 16 relative to the central shaft 14.

It will be appreciated that the connecting ends 40, 42 of the first and second arc shape clamp pieces 30, 32 need not be limited to the detachable coupling configuration shown in FIGS. 9 and 10, and other embodiments are contemplated. The first and second arc shape clamp pieces 30, 32 may include any type of first and second axially extending protrusions that circumferentially abut one another to resist flexural movement of the first and second arc shape clamp pieces 30, 32 toward each other relative to the coupling joint 46.

Figure 11:
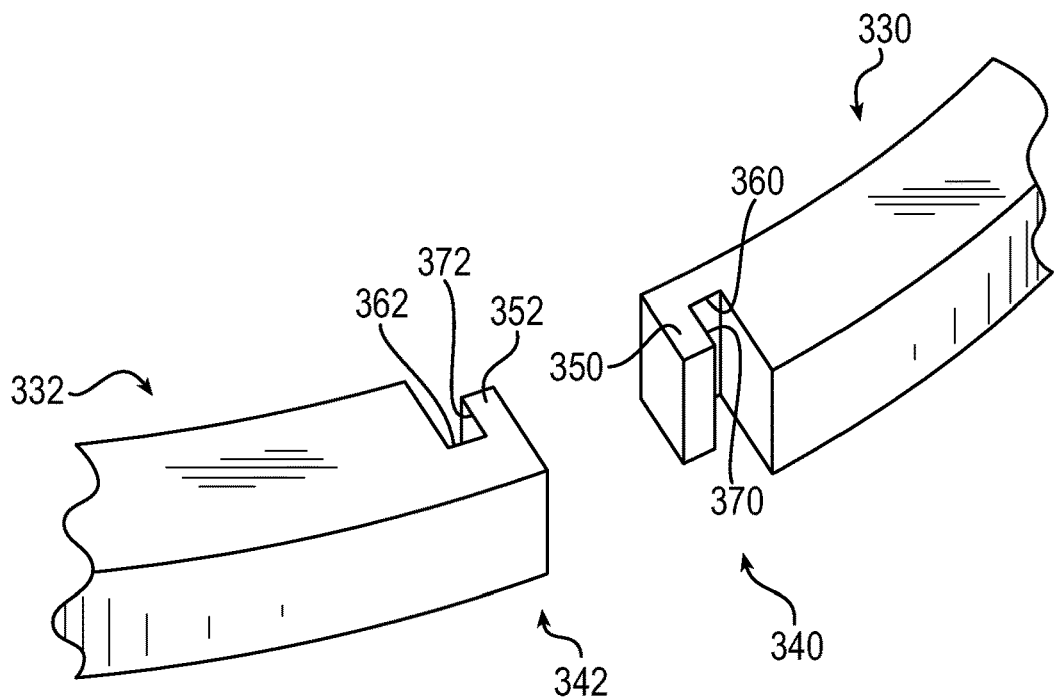
FIG. 11 is a perspective view of connecting ends of first and second arc shape clamp pieces of a brake assembly in accordance with an embodiment of the invention.

FIG. 11, for example, shows first and second arc shape clamp pieces 330, 332 in which the connecting ends 340, 342 have respective first and second axially extending tabs 350, 352 and first and second axially extending notches 360, 362 that are configured to be slidable axially and radially relative to one another. As will be appreciated, the chief difference between the FIG. 9 and FIG. 11 embodiments is that the tabs 270, 272 project axially from the circumferential portions 160, 162 in FIG. 9, and the tabs 340, 342 project radially from the circumferential portions 160, 162 in FIG. 11. The arc shape clamp pieces 330, 332 are coupled together by fitting or inserting the first axially extending tab 350 within the second axially extending notch 362, and by fitting or axially inserting the second axially extending tab 352 within the first axially extending notch 360. Once coupled together, the connecting ends 340, 342 form the aforementioned coupling joint 46 that functions as the joint relative to which the arc shape clamp pieces 330, 332 flex. During application of a frictional braking force to the central shaft 14, the axially extending tabs 350, 352 circumferentially abut one another at respective opposite facing walls 370, 372 to resist flexural movement of the first and second arc shape clamp pieces 330, 332 toward each other relative to the coupling joint 46. The greater the frictional braking force, the greater is the circumferentially abutting resistance load applied by one facing wall 370 against the opposing facing wall 372.

The axially extending notches 360, 362 have an angular width that is wider than the angular width of the axially extending tabs 350, 352. This provides an angular clearance between the tabs 350, 352 and the walls of the notches 360, 362 to facilitate fitting or insertion of the tabs 350, 352 within the respective notches 360, 362, and thus easy assembly of the interlocking split that forms the coupling joint 46. The radially protruding tabs 180, 182 are then positioned in the hub notch 186. In one form, in the initial assembly of the interlocking split and insertion of the tabs 180, 182 in the hub notch 186, the axially extending tabs 350, 352 may be circumferentially separate from one another such that the arc shape clamp pieces 330, 332 are in an unflexed or relaxed state. In another form, in the initial assembly of the interlocking split and insertion of the tabs 180, 182 in the hub notch 186, the axially extending tabs 350, 352 may be in circumferentially abutting relation at the opposite facing walls 370, 372 such that the arc shape clamp pieces 330, 332 are in a slightly flexed state. In any event, the actuator 70 may then be used to urge the first and second arc shape clamp pieces 330, 332 toward one another thereby to impart the desired frictional braking force to the central shaft 14. When the first and second arc shape clamp pieces 330, 332 are urged toward each other to apply the frictional braking force to the central shaft 14, the axially extending tabs 350, 352 and thus the arc shape clamp pieces 330, 332 engage one another and form the coupling joint 46 relative to which the arc shape clamp pieces 330, 332 flex in applying the frictional braking force to the shaft 14, as above described. Similarly, when the actuator 70 is backed off, the first and second arc shape clamp pieces 330, 332 flex away from each other to decrease the frictional braking force applied to the central shaft 14.

Further, the axially extending notches 360, 362 are open at their radially opposite ends. This enables radial movement of the axially extending tabs 350, 352 such that when the first and second arc shape clamp pieces 330, 332 are urged toward each other to apply a frictional braking force to the central shaft 14, the axially extending tabs 350, 352 and thus the arc shape clamp pieces 330, 332 shift radially relative to one another and, being in circumferentially abutting relation, engage one another and form the coupling joint 46 relative to which the arc shape clamp pieces 330, 332 flex in applying the frictional braking force to the shaft 14, as above described. Similarly, when the first and second arc shape clamp pieces 330, 332 are flexed away from each other to decrease the frictional braking force applied to the central shaft 14, the axially extending tabs 350, 352 and thus the arc shape clamp pieces 330, 332 move radially relative to one another as they unflex.

Figure 12:
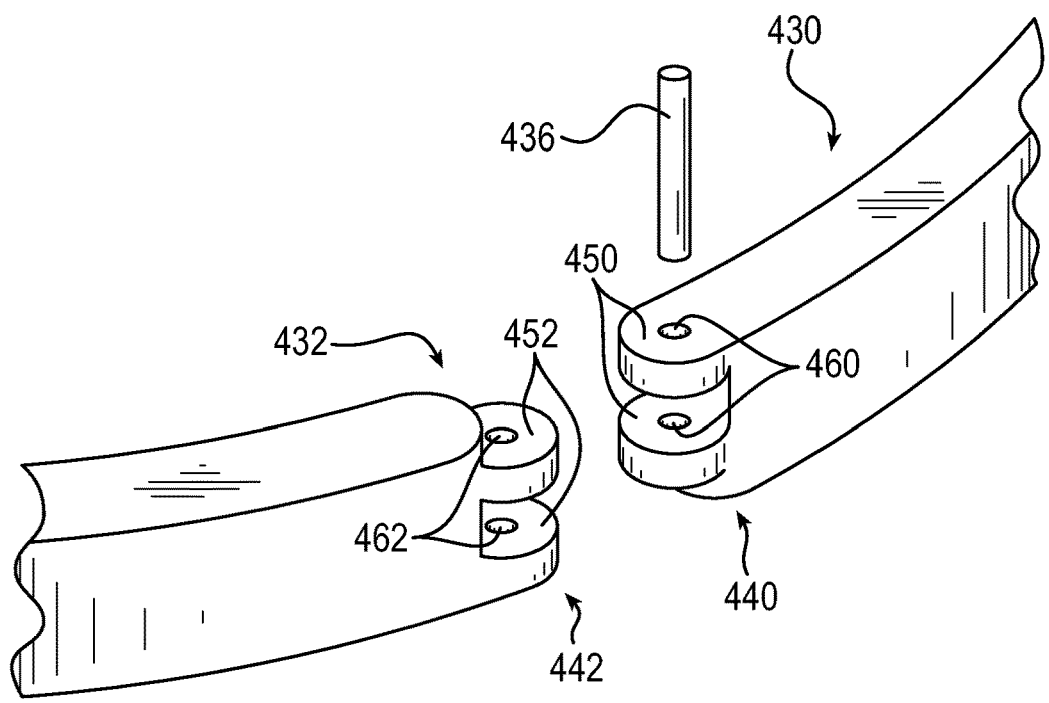
FIG. 12 is a perspective view of connecting ends of first and second arc shape clamp pieces of a brake assembly in accordance with an embodiment of the invention.

FIG. 12 shows another embodiment. Here, first and second arc shape clamp pieces 430, 432 are detachably coupled to one another by a hinge 436, a pin 436 in the illustrative embodiment, at the respective connecting ends 440, 442. The arc shape clamp pieces 430, 432 are coupled together by interlocking hinge prongs 450, 452 and sliding the pin 436 axially into holes 460, 462 in the respective prongs 450, 452. Once coupled together, the connecting ends 440, 442 form the coupling joint 46 that functions as the joint relative to which the arc shape clamp pieces 430, 432 flex. During application of a frictional braking force to the central shaft 14, the pin 436 holds the hinge prongs 450, 452 circumferentially together to resist flexural movement of the first and second arc shape clamp pieces 430, 432 toward each other relative to the coupling joint 46. The greater the frictional braking force, the greater is the resistance load by the pin 436 against the opposing hinge prongs 450, 452. As will be appreciated, axial, circumferential and radial clearances can be built into the holes 460, 462 to enable respective axial, circumferential and radial shifting between the arc shape clamp pieces 430, 432, in substantially the same manner as the embodiments of FIG. 9 and FIG. 11.

Figure 13:
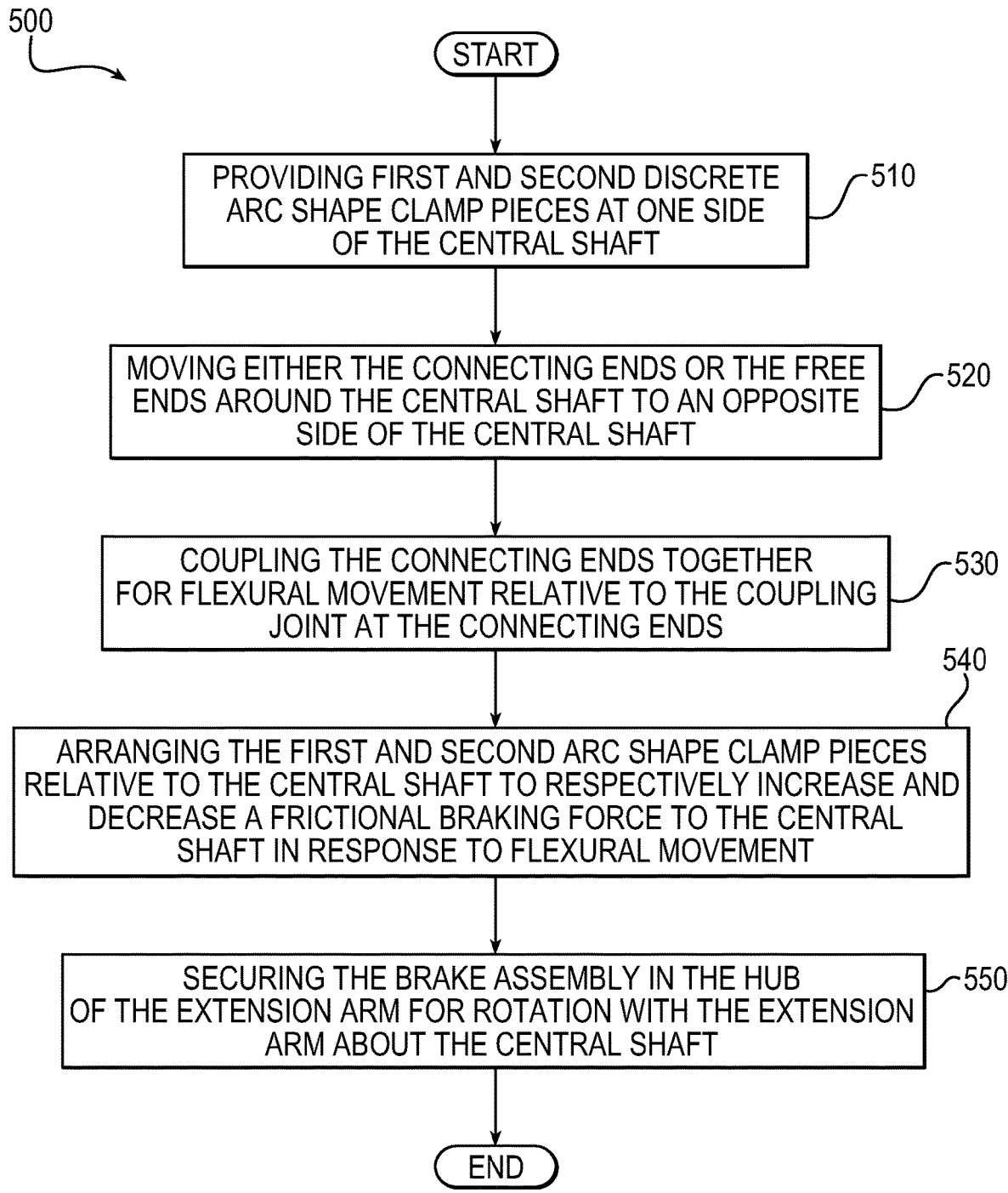
FIG. 13 shows a flowchart of a method of installing a brake assembly in a medical device support system in accordance with an embodiment of the invention.

Referring now to FIG. 13, there is shown a flowchart 500 of a method of installing a brake assembly in a medical device support system, such as the brake assembly 18 in the medical device support system 10 of FIG. 1. At step 510, the first and second discrete arc shape clamp pieces 30, 32 of the brake assembly 18 are provided at one side of the central shaft 14, for example, in a position radially outward of the central shaft 14. This may be in a health treatment room such as a surgery room, for example, where the central shaft 14 is made accessible for example by an access opening 148 as shown in FIG. 2. At step 520, either the connecting ends 40, 42 or the free ends 50, 52 of the first and second discrete arc shape clamp pieces 30, 32 are moved around the central shaft 14 to an opposite side of the central shaft 14 so that the connecting ends 40, 42 and free ends 50, 52 are situated at opposite sides of the central shaft 14. At step 530, the connecting ends 40, 42 are coupled together for flexural movement relative to the coupling joint 46 at the connecting ends 40, 42 and for free movement at the free ends 50, 52. At step 540, the first and second arc shape clamp pieces 30, 32 are arranged relative to the central shaft 14 to respectively increase and decrease a frictional braking force to the central shaft 14 in response to flexural movement of the first and second arc shape clamp pieces 30, 32 relative to the coupling joint 46. At step 550, the brake assembly 18 is secured in the hub 128 of the extension arm 16 for rotation with the extension arm 16 about the central shaft 14.

The arranging step can include arranging the first and second arc shape clamp pieces 30, 32 to form a multi-piece split collar around the central shaft 14 that is configured to contract and expand relative to the central shaft 14 in response to flexural movement of the first and second arc shape clamp pieces 30, 32 relative to the coupling joint 46. The multi-piece collar can be any number of clamp pieces and need not be limited to two clamp pieces. The coupling step can include interlocking the connecting ends 40, 42 of the first and second arc shape clamp pieces 30, 32. The coupling step can include sliding the first and second arc shape clamp pieces 30, 32 axially relative to one another, as in the embodiments of FIGS. 9 and 11. The coupling step can include hingedly connecting the connecting ends 340, 342 of the first and second arc shape clamp pieces 430, 432, as in the embodiment of FIG. 12. The method can further include mounting a retaining snap ring in a groove in the central shaft 14 to axially retain the first and second arc shape clamp pieces onto the central shaft 14.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical device support system, comprising:
a central shaft;
an extension arm having a support for a medical device and a hub at its proximal end mounted to the central shaft for pivotable movement about the central shaft; and,
a brake assembly secured in the hub for rotation therewith and including first and second discrete arc shape clamp pieces that are detachably coupled to one another at one end to form a coupling joint for flexural movement of the first and second clamp pieces relative to the coupling joint and that are free at an opposite end;
wherein the brake assembly includes an actuator configured to flex the first and second clamp pieces relative to the coupling joint toward and away from each other to respectively increase and decrease a frictional braking force to the central shaft.

2. The medical device support system of claim 1, wherein the first and second arc shape clamp pieces form a multi-piece split collar around the central shaft that is configured to contract and expand relative to the central shaft in response to flexural movement of the first and second arc shape clamp pieces relative to the coupling joint.

3. The medical device support system of claim 1, wherein when the first and second clamp pieces are flexed toward each other to increase the frictional braking force to the central shaft, the first and second clamp pieces have an arc shape contact with the outer periphery of the central shaft.

4. The medical device support system of claim 1, wherein the brake assembly is configured to operate in a passive manner, preventing motion of the extension arm relative to the central shaft by means of the frictional braking force, wherein the frictional braking force can be overcome by a user pushing on the extension arm.

5. The medical device support system of claim 1, wherein the first and second arc shape clamp pieces are diametrically opposed from one another on opposite sides of the central shaft.

6. The medical device support system of claim 1, wherein the medical device is a surgical light.

7. The medical device support system of claim 1, wherein the first and second arc shape clamp pieces include respective liners made of a material selected from polyolefins, polyesters, acetals, polyamides, fluorinated polymers, vinyls, acrylics, polycarbonates, polyimides, polysulphones, and blends and alloys thereof.

8. The medical device support system of claim 1, wherein the first and second arc shape clamp pieces include unreinforced, semi-crystalline thermoplastic polyester based on polyethylene terephthalate (PET-P).

9. The medical device support system of claim 1, wherein the first and second arc shape clamp pieces include respective first and second polymer liners made of UHMW-PE.

10. A brake assembly for a medical device support system having a central shaft, the brake assembly comprising:
first and second discrete arc shape clamp pieces that are detachably coupled to one another at one end to form a coupling joint for flexural movement of the first and second clamp pieces relative to the coupling joint and that are free at an opposite end,
wherein the first and second arc shape clamp pieces are configured to flex relative to the coupling joint toward and away from each other to respectively increase and decrease a frictional braking force to the central shaft.

11. The brake assembly of claim 10, wherein the first and second arc shape clamp pieces form a multi-piece split collar around the central shaft that is configured to contract and expand relative to the central shaft in response to flexural movement of the first and second arc shape clamp pieces relative to the coupling joint.

12. The brake assembly of claim 10, wherein the first and second arc shape clamp pieces are detachably coupled to one another by being interlocked to each other at the one end.

13. The brake assembly of claim 10, wherein the one ends of the first and second arc shape clamp pieces include respective first and second axially extending protrusions that circumferentially abut one another to resist flexural movement of the first and second arc shape clamp pieces toward each other relative to the coupling joint.

14. The brake assembly of claim 10, wherein the one ends of the first and second arc shape clamp pieces have respective first and second axially extending tabs and first and second axially extending notches, and the first axially extending tab fits within the second axially extending notch and the second axially extending tab fits within the first axially extending notch.

15. The brake assembly of claim 10, wherein the one ends of the first and second arc shape clamp pieces are slidable axially and radially relative to one another.

16. The brake assembly of claim 10, wherein the first and second arc shape clamp pieces are detachably coupled to one another by a hinge at the one end.

17. The brake assembly of claim 10, wherein the first and second arc shape clamp pieces have an identical geometry.

18. A method of installing a brake assembly in a medical device support system having a central shaft, the method comprising:
providing first and second discrete arc shape clamp pieces of the brake assembly, wherein the first and second arc shape clamp pieces each have a connecting end and a free end;
moving either the connecting ends or the free ends around the central shaft so that the connecting ends are situated at one side of the central shaft and the free ends are situated at an opposite side of the central shaft;
coupling the connecting ends of the first and second arc shape clamp pieces together to form a coupling joint for flexural movement of the first and second clamp pieces relative to the coupling joint at the connecting ends and for free movement at the free ends;
arranging the first and second arc shape clamp pieces relative to the central shaft to respectively increase and decrease a frictional braking force to the central shaft in response to flexural movement of the first and second arc shape clamp pieces relative to the coupling joint; and,
securing the brake assembly in a hub of an extension arm for rotation with the extension arm about the central shaft.

19. The method of claim 18, wherein the arranging includes arranging the first and second arc shape clamp pieces to form a multi-piece split collar around the central shaft that is configured to contract and expand relative to the central shaft in response to flexural movement of the first and second arc shape clamp pieces relative to the coupling joint.

20. The method of claim 18, wherein the coupling includes interlocking the connecting ends of the first and second arc shape clamp pieces.

21. The method of claim 18, wherein the coupling includes sliding axially the first and second arc shape clamp pieces relative to one another.

22. The method of claim 18, wherein the coupling includes hingedly connecting the connecting ends of the first and second arc shape clamp pieces.

* * * * *